United States Patent
Dryer

[19]

[11] Patent Number: 6,135,279
[45] Date of Patent: Oct. 24, 2000

[54] SANITIZING TOOTHBRUSH HOLDER

[76] Inventor: Richard Dryer, 29400 SW. 17th Ave., Homestead, Fla. 33030

[21] Appl. No.: 09/444,894

[22] Filed: Nov. 22, 1999

[51] Int. Cl.[7] ........................................................ A61L 2/18
[52] U.S. Cl. .................. 206/362.1; 206/15.2; 206/209.1; 206/804; 422/301
[58] Field of Search ................................... 134/201, 900; 206/15.2, 209, 209.1, 362.1, 804; 312/206; 422/28, 301

[56] References Cited

U.S. PATENT DOCUMENTS

| | | | |
|---|---|---|---|
| 1,361,842 | 12/1920 | Evslin | 312/206 |
| 3,904,362 | 9/1975 | DiPaolo | 206/209 |
| 4,915,219 | 4/1990 | Ottimo . | |
| 4,997,629 | 3/1991 | Marchand et al. . | |
| 5,377,824 | 1/1995 | Seymour . | |
| 5,566,823 | 10/1996 | Summers . | |
| 5,690,214 | 11/1997 | Gaines et al. . | |

*Primary Examiner*—Jim Foster
*Attorney, Agent, or Firm*—Michael I Kroll

[57] ABSTRACT

The present invention 10 discloses a sanitizing toothbrush holder comprising a container 12 having at least a pair of compartments 32 therein for receiving removable platforms 26 upon which the toothbrushes 18 rest. The platforms 26 are connected by downwardly extending rod-like members 44 to a closure means or lid 24 of the container. The closure means 24 is connected to and operates on a central post 40 which slidably operates inside a central aperture 46 of the container. Further, a frame-like member 28 is provided to rest on pin members 30 disposed on the members 44 which has the purpose of maintaining the toothbrush handles 18 on the platforms 26 when the entire mechanism is removed from container 12. Embodiments are shown adapted for use with two to four toothbrushes 18.

12 Claims, 9 Drawing Sheets

SANITIZING TOOTHBRUSH HOLDER

BACKGROUND OF THE INVENTION

1. Field of the Invention

The present invention relates generally to sanitizing toothbrush holders and, more specifically, to a container which may be compartmentalized having closure means, having slidable retraction means for retrieving previously deposited toothbrushes from therein, and having hinged platform means for supporting the toothbrush while being extracted. In addition in a compartmentalized extraction means said compartment can be tapered from a larger annular opening to a smaller distal base causing said toothbrush handle to move away from the extraction means as said toothbrush is extracted from said sanitizing container. Further said hinged toothbrush platform support means having connection means with said closure means whereby said closure means will be used to provide access to said toothbrushes.

Furthermore, having a retaining ring assembly which fits into a recess at the top of the receptacle providing means for completely removing the lid and attached slidable extractor member without necessitating the removal of each toothbrush individually. The slidable extractor member will support each toothbrush handle preventing it from falling to the side when the extractor member is removed completely from the receptacle for the purpose of changing the sanitizing solution or for cleaning the receptacle.

2. Description of the Prior Art

There are other toothbrush storage device designed for sanitizing toothbrushes. Typical of these is U.S. Pat. No. 5,690,214 issued to Gaines et al. on Nov. 25, 1997.

Another patent was issued to Summers on Oct. 22, 1996 as U.S. Pat. No. 5,566,823. Yet another U.S. Pat. No. 5,377,824 was issued to Seymour on Jan. 3, 1995. Another was issued on Mar. 5, 1991 to Marchand as U.S. Pat. No. 4,997,629 and still yet another patent was issued to Ottimo on Apr. 10, 1990 as U.S. Pat. No. 4,915,219.

U.S. Pat. No. 5,690,214

Inventor: Dennis Morgan Gaines et al.

Issued: Nov. 25, 1997

A device that stores and sanitizes toothbrushes in individual storage pockets in a vessel containing a sanitizing solution. Each storage pocket is formed in the top surface of the vessel in such a manner that the storage pocket is partially filled with sanitizing solution and in normal use, the pocket is sealed from the sanitizing fluid contained in the main vessel. When the sanitizing solution has served its useful life in the pockets of the vessel, the vessel is overturned, the used sanitizing liquid in each of the pockets is dumped out by over-turning the vessel. The vessel is then returned to its normal orientation, and the top of the vessel is raised slightly to allow the top of each pocket to slightly separate from the lower portion of each pocket to allow the sanitizing liquid in the vessel to flow into each pocket to replenish the sanitizing fluid in each pocket. When each pocket is filled to the desired level, the top of the vessel is returned to its sealing position and locked in this position until the solution in the pockets is spent.

U.S. Pat. No. 5,566,823

Inventor: Shirley F. Summers

Issued: Oct. 22, 1996

A sanitary holder for storing toothbrushes in a tray with a plurality of separate receptacles for holding a liquid antiseptic into which a bristle end of a toothbrush is immersed. The tray is stored in a container with a cap and is slid in and out of the container with a handle attached to the tray.

U.S. Pat. No 5,377,824

Inventor: Clyde O. Seymour

Issued: Jan. 3, 1995

A container for the storage of toothbrushes in an antiseptic liquid comprising: a container having a circular bottom wall, an annular upper opening, and a side wall therebetween, the side wall having an annular lower extent and an annular upper extent and a curved intermediate extent therebetween, the upper extent terminating in external threads; a cap having an upper circular surface and downwardly extending side walls in an annular configuration with internal threads matable with the external threads of the container; a plurality of apertures formed in a circular surface of the cap of a sufficient size to receive and allow passage of the bristle end of a toothbrush therethrough; a handle in a cylindrical configuration extending upwardly from the center of the cap between the apertures; and a rotatable cover positionable over the cap, the cover having a circular surface and downwardly extending side walls terminating in inwardly directed flanges received in a first annular recess formed in the cap and a second annular recess formed in the cover for receiving the handle of the cap.

U.S. Pat. No. 4,997,629

Inventor Paul Marchand et al.

Issued: Mar. 5, 1991

An assembly for the disinfectant of one or more toothbrushes or like objects comprising a housing generally in the form of a canister for the containment of a supply of disinfectant composition preferably in fluid form wherein an applicator chamber is formed within the housing and the toothbrushes are also oriented thereinsuch that the head and bristle portion thereof are disposed within the applicator chamber in fluid communication with disinfectant issuing from the supply. The disinfectant supply may be in the form of a pressurized aerosol container or any other applicable supply container and pump combination.

U.S. Pat. No. 4,915,219

Inventor Anthony Ottimo

Issued: Apr. 10, 1990

The disinfecting toothbrush container for holding the tooth brush and disinfecting the bristles of the toothbrush comprises a container body having a plurality of container chambers formed by dividing the container body by a plurality of substantially vertical container chamber walls. The container chambers are divided transversely by a substantially transverse flexible rubber partition having a slit in each of the container chambers large enough for insertion of the tooth brush. The transverse flexible partition divides each container chamber into an upper portion containing air and a lower portion containing a disinfecting liquid. The lips of each of the slits are firm enough to prevent dirt and germs from the air from entering the disinfecting liquid and flexible enough to sneeze the disinfecting liquid from the bristles of the toothbrush when the toothbrush is drawn through the slit. A reusable lid which can provide a liquid-tight closure is also provided.

While these toothbrush storage device may be suitable for the purposes for which they were designed, they would not be as suitable for the purposes of the present invention, as hereinafter described.

SUMMARY OF THE PRESENT INVENTION

The present invention discloses a sanitizing toothbrush holder comprising a container having at least a pair of compartments therein for receiving removable platforms upon which the toothbrushes rest. The platforms are connected by downwardly extending rod-like members to a closure means or lid for the container. The closure means is connected to and operates on a central post which slidably operates inside a central aperture of the container. Further, a frame-like member is provided to rest on pin members disposed on the rod-like members which have the purpose of maintaining the toothbrush handles on the platforms when the entire mechanism is removed from container. Embodiments are shown adapted for use with two to four toothbrushes.

A primary object of the present invention is to provide a container which may be used to store one or more toothbrushes in a disinfectant solution.

Another object of the present invention is to provide a container which may be used to store one or more toothbrushes in a disinfectant solution having closure means which seals said container from contamination from particle matter.

Yet another object of the present invention is to provide a container which may be used to store one or more toothbrushes in a disinfectant solution having closure means connected to the extraction means.

Still yet another object of the present invention is to provide a container which may be used to store one or more toothbrushes in a disinfectant solution having extraction means connected to the hinged toothbrush support means.

Another object of the present invention is to provide a container which can be used to store one or more toothbrushes in a disinfectant solution whereby all the toothbrushes can be removed from said container at the same time.

Yet another object of the present invention is to provide a slidably extractor member which will support the toothbrush handles at a predetermined point as the extractor assembly is removed from the container.

Yet another object of the present invention is to provide an additional element for larger containers which may be used to store one or more toothbrushes in a disinfectant solution having rotational means for selectively positioning said container before engaging said extraction means.

Additional objects of the present invention will appear as the description proceeds.

The present invention overcomes the shortcomings of the prior art by providing a container which may be compartmentalized having closure means, having slidable retraction means for retrieving previously deposited toothbrushes from therein, having rotational means for selectively positioning said container while extracting a toothbrush from therein and having hinged platform means for supporting the toothbrush while being extracted. In addition in a compartmentalized extraction means said compartment can be tapered from a larger annular opening to a smaller distal base causing said toothbrush handle to move away from the extraction means as said toothbrush is extracted from said sanitizing container. Further said hinged toothbrush platform support means having connection means with said closure means whereby said closure means will be used to provide access to said toothbrushes.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

The extraction mechanism is comprised of a lid which forms closure means for protecting the contents from particle matter falling into the compartments. In addition there is a central guide post which is inserted into a central housing aperture. Also, the extraction mechanism has a number of posts equal to the number of compartments within the sanitizing toothbrush housing. Each of these has a pin-like projection for engaging the slidable extension retention member which prevents the toothbrushes from falling out as the extraction mechanism is raised. Each of these post has a toothbrush platform support on the distal end. The hinged toothbrush platform support hinge member will engage the outer housing wall while being inserted into or extracted from said sanitizing toothbrush housing but does not fully open.

Figure 6:
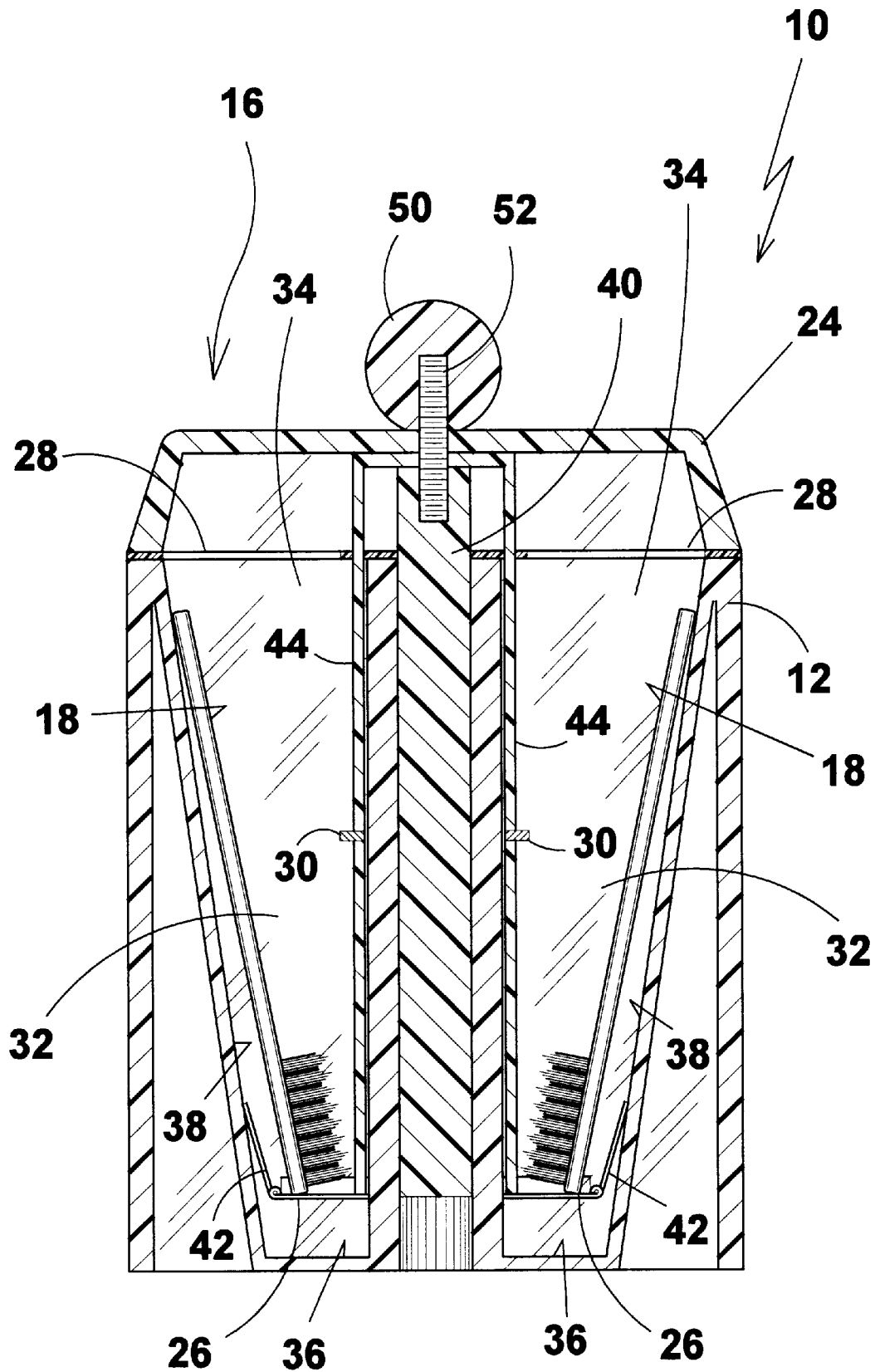

FIG. 6 is a sectional view of the present invention. Shown is the sanitizer toothbrush holder having a compartmentalized housing member which forms a receptacle for the extraction mechanism. The extraction mechanism is comprised of a lid which forms closure means for protecting the contents from particle matter falling into the compartments. In addition there is a central guide post. Also, the extraction mechanism has a plurality of posts equal to the number of compartments within the sanitizing toothbrush holder. Each of these has a pin-like projection for engaging the slidable extension retention member which prevents the toothbrushes from falling out as the extraction mechanism is raised. Each of these post has a toothbrush platform support on the distal end. The hinged toothbrush platform support member will engage the outer housing wall of the toothbrush container while being inserted into or extracted from said sanitizing toothbrush housing member due to the hinged platform. The individual toothbrush containers have a tapered annular opening and a smaller tapered base whereby the toothbrushes will diverge from the extraction mechanism while being raised.

Figure 7:
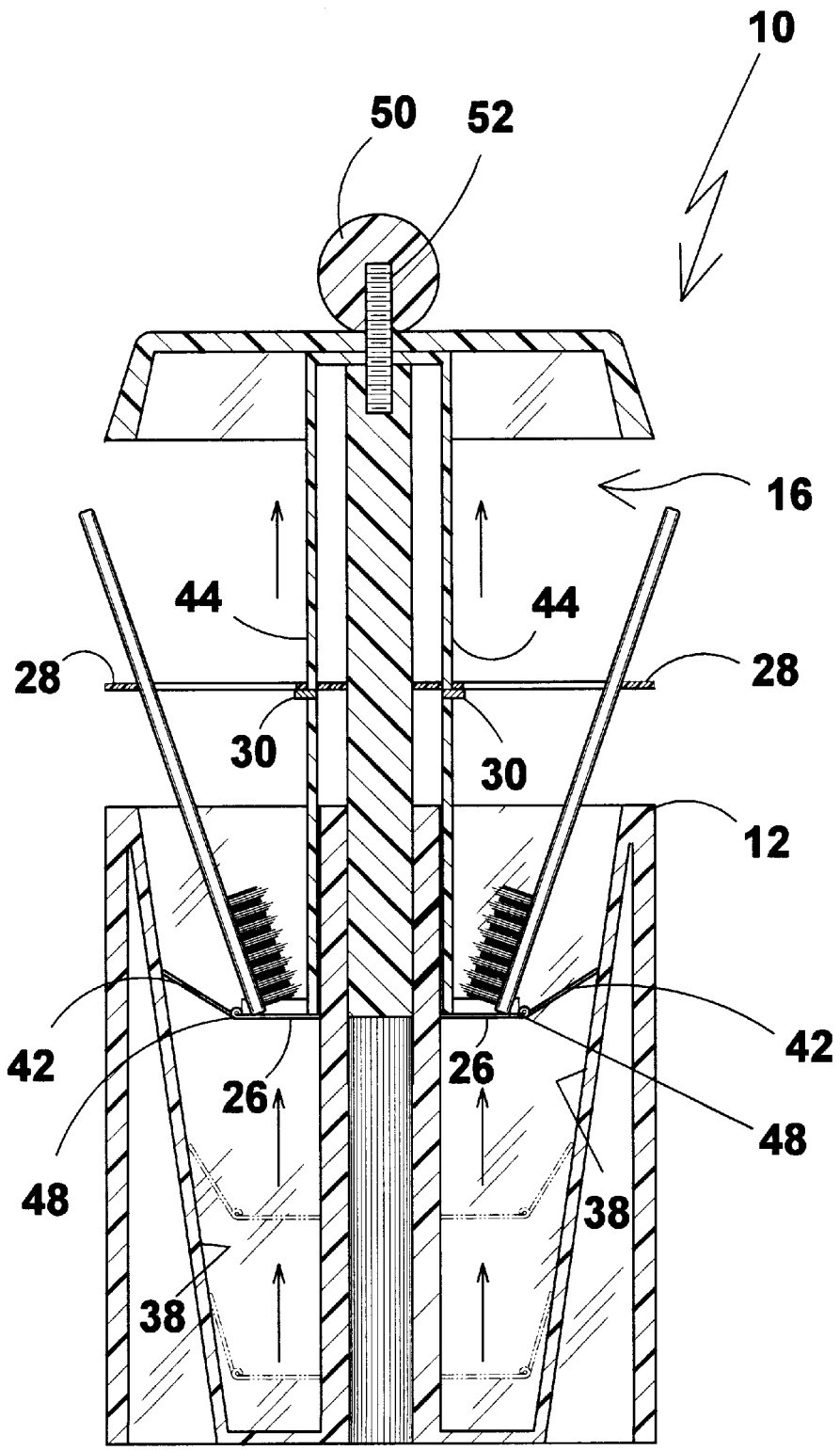

FIG. 7 is a sectional view of the present invention. Shown is the extraction mechanism partially raised from the compartmentalized housing member having the slidable extraction retention member engaged by pin-like projection attached to the toothbrush post of the extraction mechanism. The individual toothbrush platform supports have hinged means for continually engaging the tapered side of the cavity. The hinge will deploy to a fixed position forming a back support for the toothbrush if said extractor mechanism is removed from the container housing.

Figure 8:
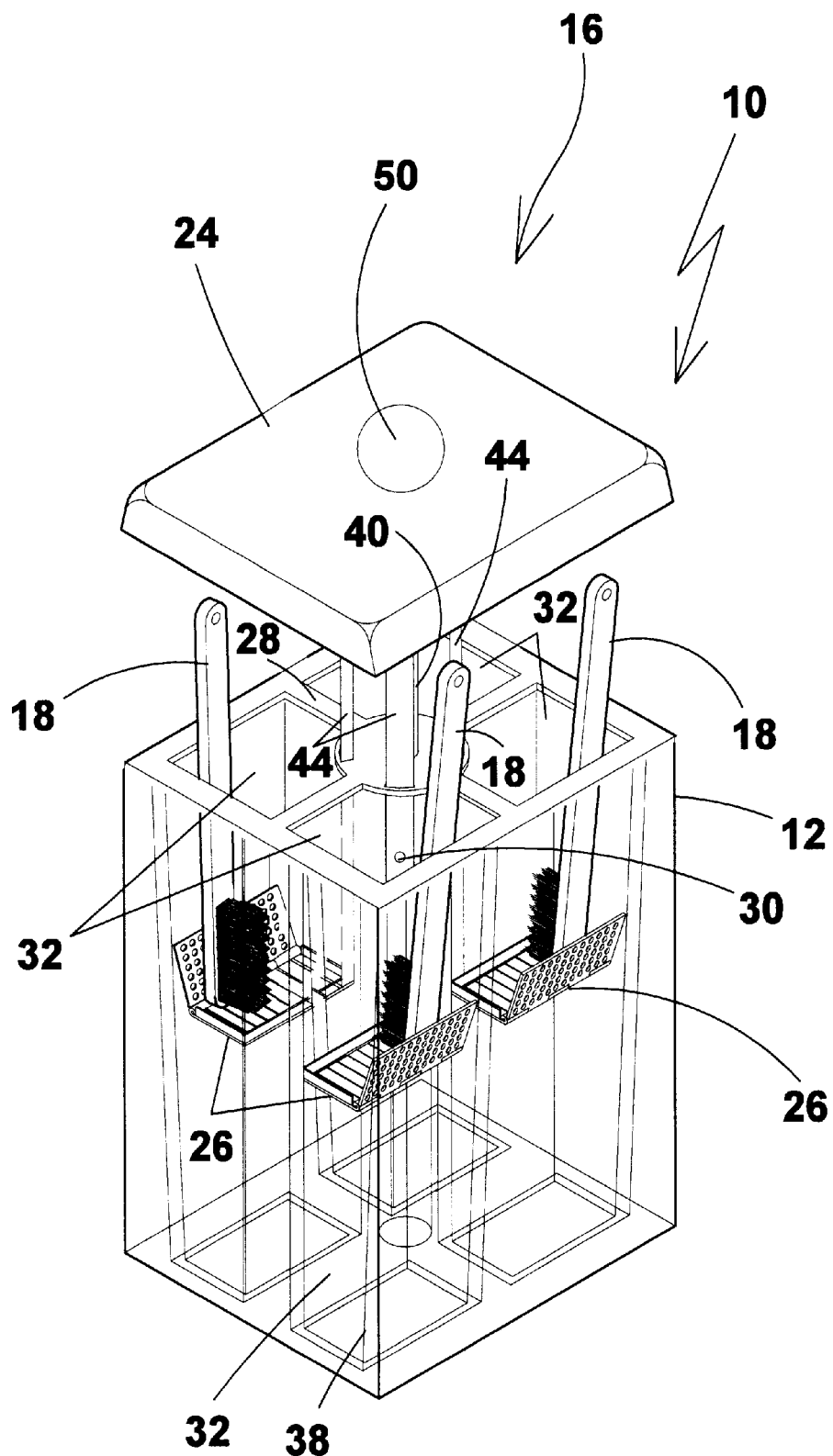

FIG. 8 is a perspective view of the present invention having additional elements. Shown is the sanitizing toothbrush holder having a plurality of sanitizing toothbrush compartments. Also shown is the extraction mechanism in the partially raised position having a lid which forms closure means for protecting the contents from particle matter falling into the compartments. In addition there is a central guide post. Also, the extraction mechanism has a plurality of posts equal to the number of compartments within the sanitizing toothbrush holder. Each of these has a pin-like projection for engaging the slidable extension retention member which prevents the toothbrushes from falling out as the extraction mechanism is raised. Each of these post has a toothbrush platform support on the distal end. The hinged toothbrush platform support member will engage the outer housing wall of the toothbrush container while being inserted into or extracted from said sanitizing toothbrush housing member due to the hinged platform. The individual toothbrush containers have a tapered annular opening and a smaller tapered base whereby the toothbrushes will diverge from the extraction mechanism while being raised.

Figure 9:
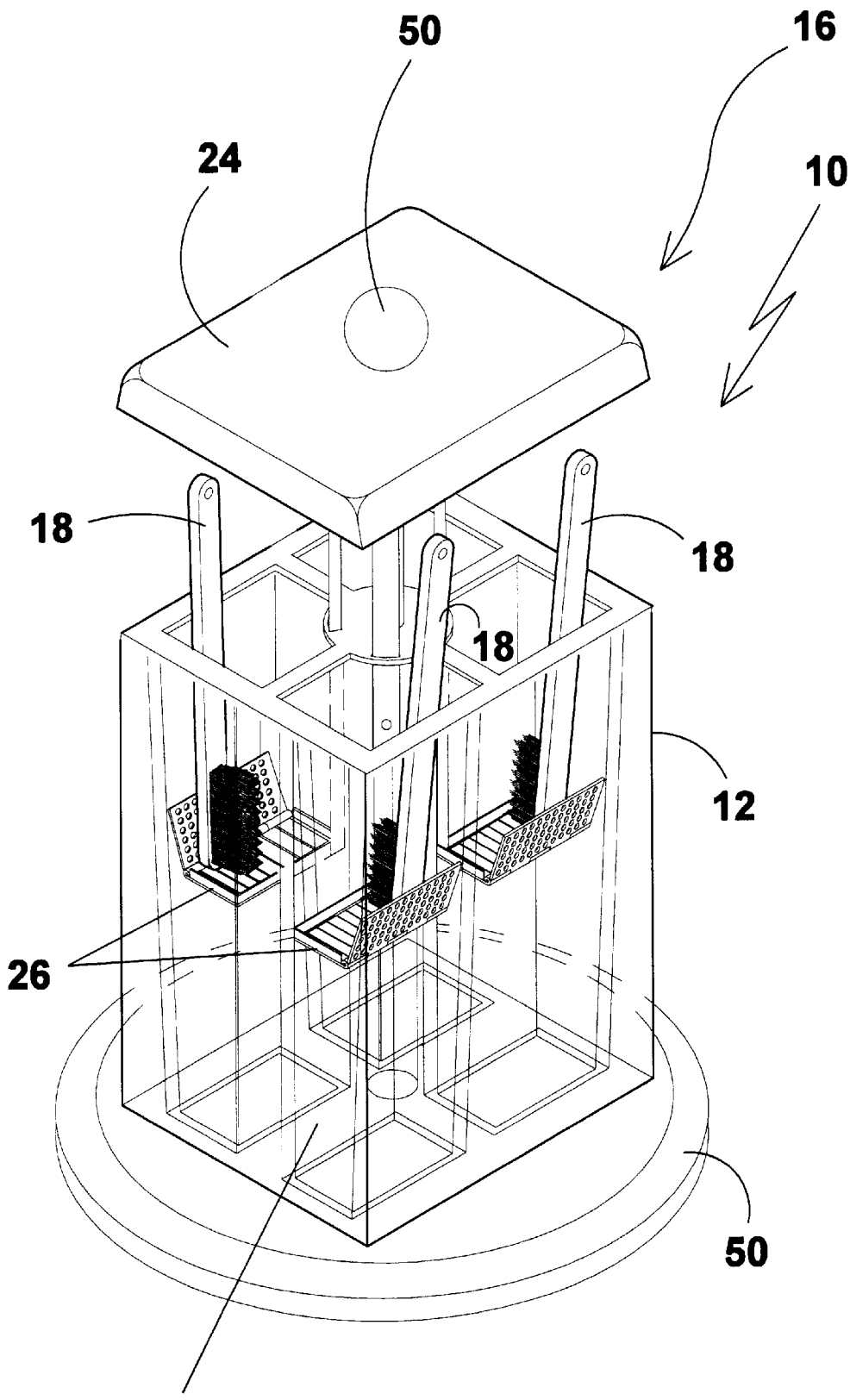

FIG. 9 is a perspective view of the present invention having additional elements. Shown is a sanitizing toothbrush holder having a plurality of toothbrushes in segregated compartments. The toothbrushes are individually retrieved by raising the extractor mechanism which is comprised of a lid which forms closure means for protecting the contents from particle matter falling into the compartments. In addition there is a central guide post. Also, the extraction mechanism has a plurality of posts equal to the number of compartments within the sanitizing toothbrush holder. Each of these has a pin-like projection for engaging the slidable extension retention member which prevents the toothbrushes from falling out as the extraction mechanism is raised. Each of these post has a toothbrush platform support on the distal end. The hinged toothbrush platform support member will engage the outer housing wall of the toothbrush container while being inserted into or extracted from said sanitizing toothbrush housing member due to the hinged platform. The individual toothbrush containers have a tapered annular opening and a smaller tapered base whereby the toothbrushes will diverge from the extraction mechanism while being raised. Also the container which rests on a base member can be rotated to selectively position a particular toothbrush.

LIST OF REFERENCE NUMERALS

With regard to reference numerals used, the following numbering is used throughout the drawings.

10 present invention

12 container 14 disinfectant
16 extractor mechanism
18 toothbrush
20 toothbrush handle
22 connection means
24 closure means
26 platform
27 three-sided rim
28 extraction retention member
30 pin member
32 individual toothbrush container
34 opening
36 base
38 outer wall
40 center post
hinged means
post
central aperture
hinge
knob
knob connecting means

DESCRIPTION OF THE PREFERRED EMBODIMENT(S)

In order that the invention may be more fully understood, it will now be described, by way of example, with reference to the accompanying drawings in which FIGS. 1 through 9 illustrate the present invention being a sanitizing toothbrush holder.

Figure 1:
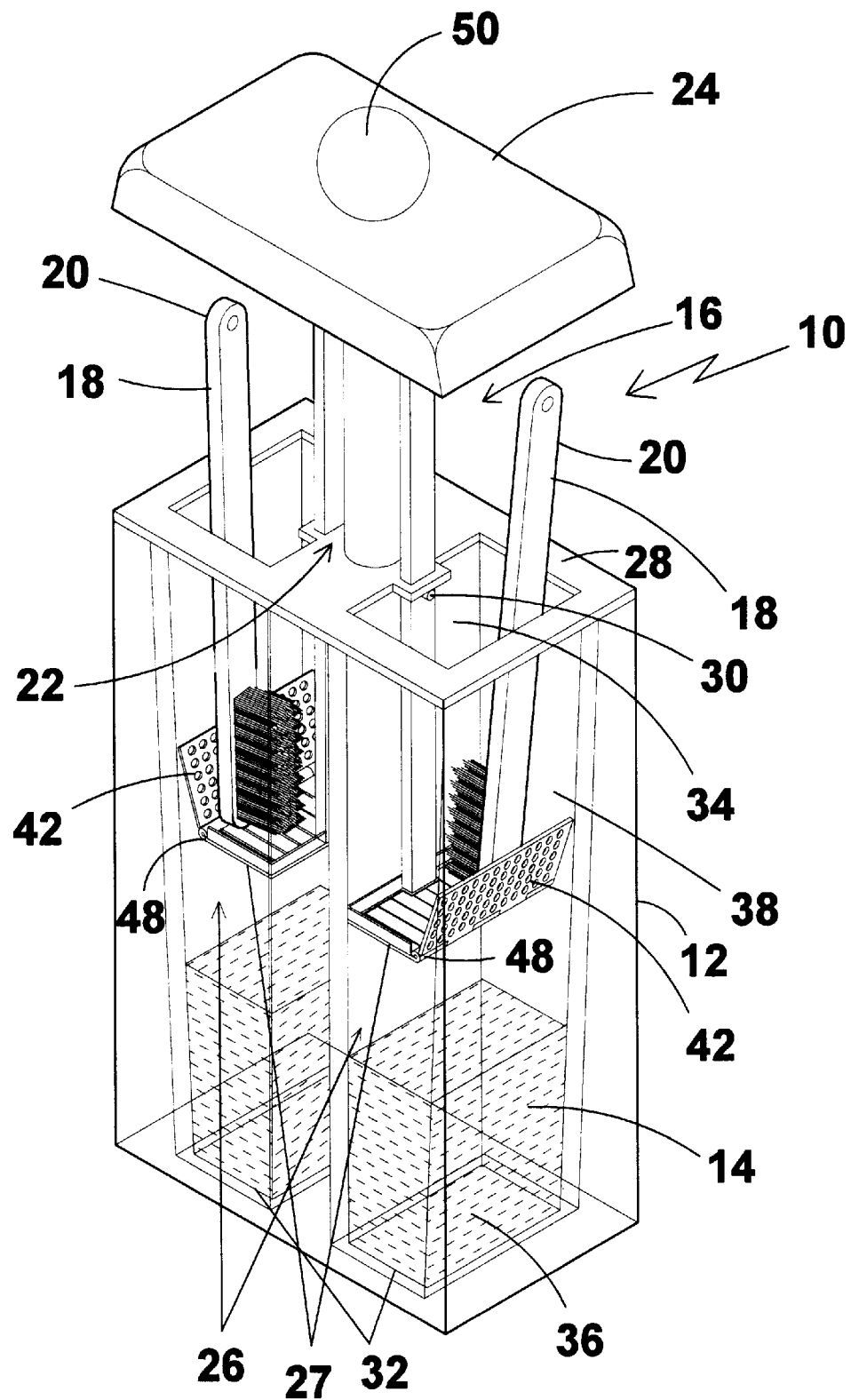
FIG. 1 is a perspective view of the present invention. Shown is a container having an amount of disinfectant therein having the extractor mechanism in a partially raised position wherein said toothbrushes can be selectively removed by the toothbrush handle. The extraction mechanism has connection means with the closure means and the hinged toothbrush platform support. Additionally shown is a slidable extraction retention member engaged by a pin-like projection. Whereby should further lateral movement of the extractor mechanism occur the extraction retention member will prevent the toothbrushes from falling off of the toothbrush platform supports. The individual toothbrush containers have a tapered annular opening and a smaller tapered base whereby said toothbrushes will diverge from the extraction mechanism while being raised. The hinged toothbrush platform support member will engage the outer housing wall of the toothbrush container while being inserted into or extracted from said container due to the hinged platform.

Turning to FIG. 1, shown therein is a perspective view of the present invention 10. Shown is a container or housing 12 having an amount of disinfectant 14 therein having the extractor mechanism 16 in a partially raised position wherein the toothbrushes 18 can be selectively removed by the toothbrush handle 20. The extraction mechanism 16 has connection means 22 between the closure means 24 with knob 50 and the hinged toothbrush platform support 26. Additionally shown is a slidable extraction retention member 28 engaged by a pin-like projection 30, whereby should further lateral movement of the extractor mechanism occur the extraction retention member 28 will prevent the toothbrushes 18 from falling off of the toothbrush platform supports 26. The individual toothbrush containers 32 have a tapered annular opening 34 and a smaller tapered base 36 whereby the toothbrushes 18 will diverge from the extraction mechanism 16 while being raised. The hinged means 42 on the toothbrush platform support member 26 will engage the outer housing wall 38 of the toothbrush container 32 while being inserted into or extracted from the container due to the hinges 48 on platform 26. Platform 26 has a three-sided rim 27 thereon for containing the toothbrush 20 therein.

Figure 2:
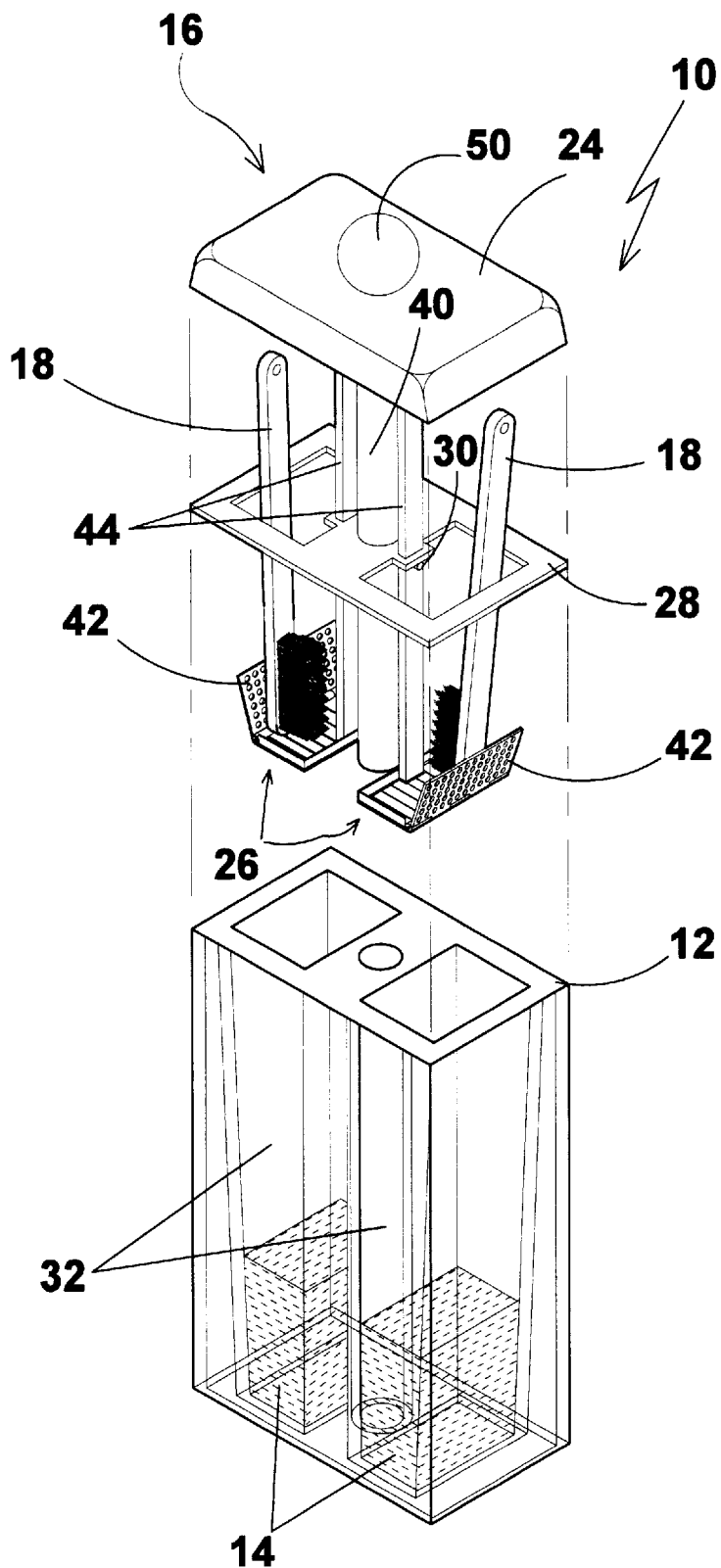
FIG. 2 is a perspective view of the present invention. Shown is the extraction mechanism removed from the container housing member which has an amount of disinfectant contained therein. The extraction mechanism has connection means with the closure means and the hinged toothbrush platform support. Additionally having a slidable extraction retention member engaged by a pin-like projection attached to the central post of the extraction mechanism. Which engages the extraction retention member as a predetermined point to retain the toothbrushes with the extraction member. The individual toothbrush platform supports have hinged means for continually engaging the tapered side of the cavity. The hinge will deploy to a fixed position forming a back support for the toothbrush while said extractor mechanism is removed from the container housing.

Turning to FIG. 2, shown therein is a perspective view of the present invention 10. Shown is the extraction mechanism 16 removed from the container 12 housing member which has an amount of disinfectant 14 contained therein. The extraction mechanism 16 has connection means 44 with the closure means 24 and the hinged toothbrush platform support 26. Also shown is a slidable extraction retention member 28 engaged by a pin-like projection 30 attached to the central post 40 of the extraction mechanism 16 which engages the extraction retention member frame 28 at a predetermined elevation point to retain the toothbrushes 18 within the extraction member 16. The individual toothbrush platform supports 26 have hinged means 42 for continually engaging the tapered side of the cavity 32. The hinge means 42 will deploy to a fixed position forming a back support for the toothbrush 18 while said extractor mechanism 16 is removed from the container housing 12.

Figure 3:
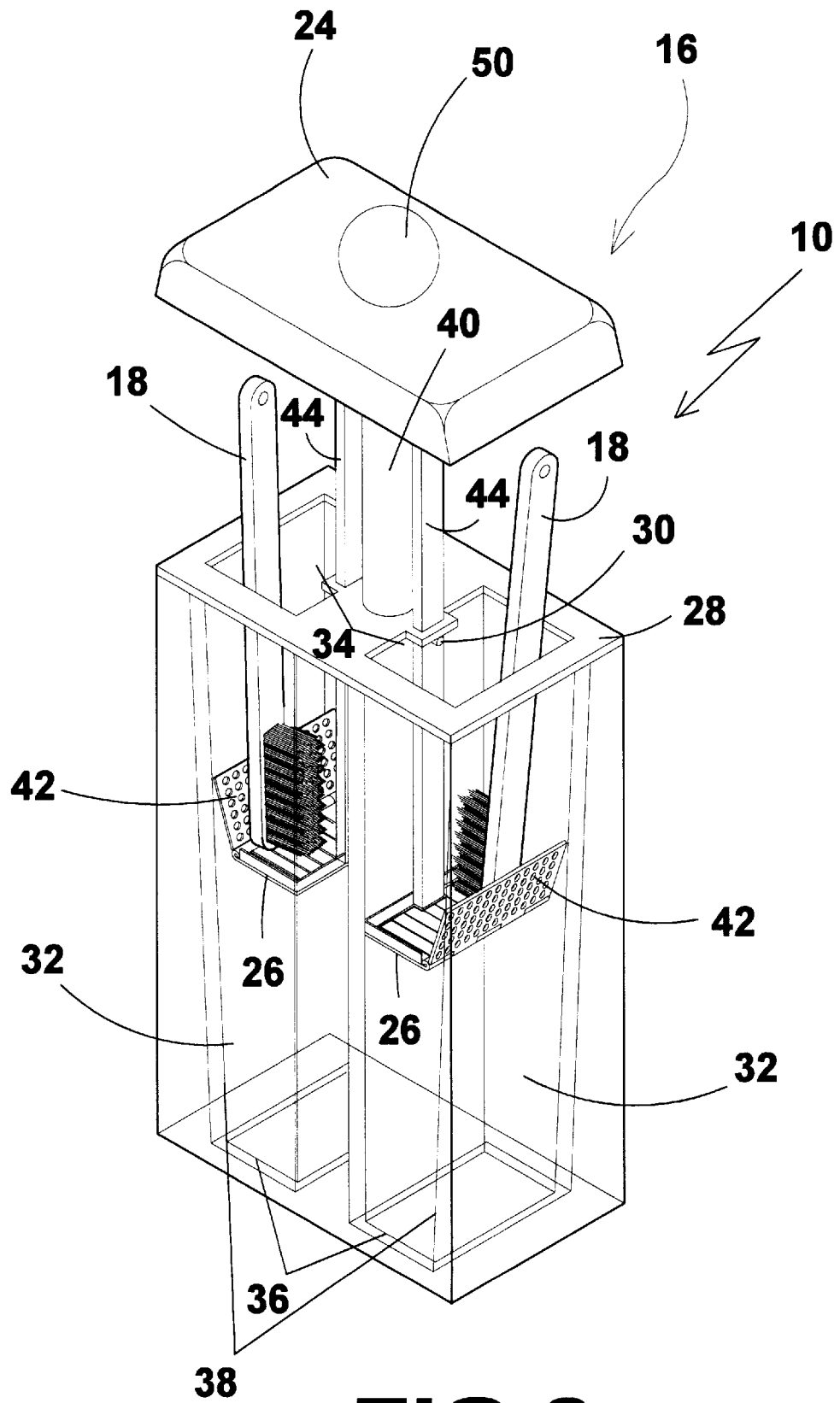
FIG. 3 is a perspective view of the present invention. Shown is the sanitizing toothbrush holder having the extractor mechanism in a partially raised position. The extraction mechanism is comprised of a lid which forms closure means for protecting the contents from particle matter falling into the compartments. In addition there is a central guide post. Also, the extraction mechanism has a plurality of posts equal to the number of compartments within the sanitizing toothbrush holder. Each of these has a pin-like projection for engaging the slidable extension retention member which prevents the toothbrushes from falling out as the extraction mechanism is raised. Each of these post has a toothbrush platform support on the distal end. The hinged toothbrush platform support member will engage the outer housing wall of the toothbrush container while being inserted into or extracted from said sanitizing toothbrush housing member due to the hinged platform. The individual toothbrush containers have a tapered annular opening and a smaller tapered base whereby the toothbrushes will diverge from the extraction mechanism while being raised.

Turning to FIG. 3, shown therein is a perspective view of the present invention 10. Shown is the sanitizing toothbrush holder having the extractor mechanism 16 in a partially raised position. The extraction mechanism 16 is comprised of a lid 24 which forms closure means for protecting the contents from particle matter falling into the compartments 32. In addition, there is a central guide post 40. Also, the extraction mechanism 16 has a plurality of posts 44 equal to the number of compartments within the sanitizing toothbrush holder 10. Each of these has a pin-like projection 30 for engaging the slidable extension retention member frame 28 which prevents the toothbrushes 18 from falling out as the extraction mechanism 16 is raised. Each of these posts 44 has a toothbrush platform support 26 disposed on the distal end. The hinged means 42 of the toothbrush platform support member 26 will engage the outer housing wall 38 of the toothbrush container 32 while being inserted into or extracted from the sanitizing toothbrush housing member due to the hinged platform 26. The individual toothbrush containers 32 have a tapered annular opening 34 and a smaller tapered base 36 whereby the toothbrushes 18 will diverge from the extraction mechanism 16 while being raised.

Figure 4:
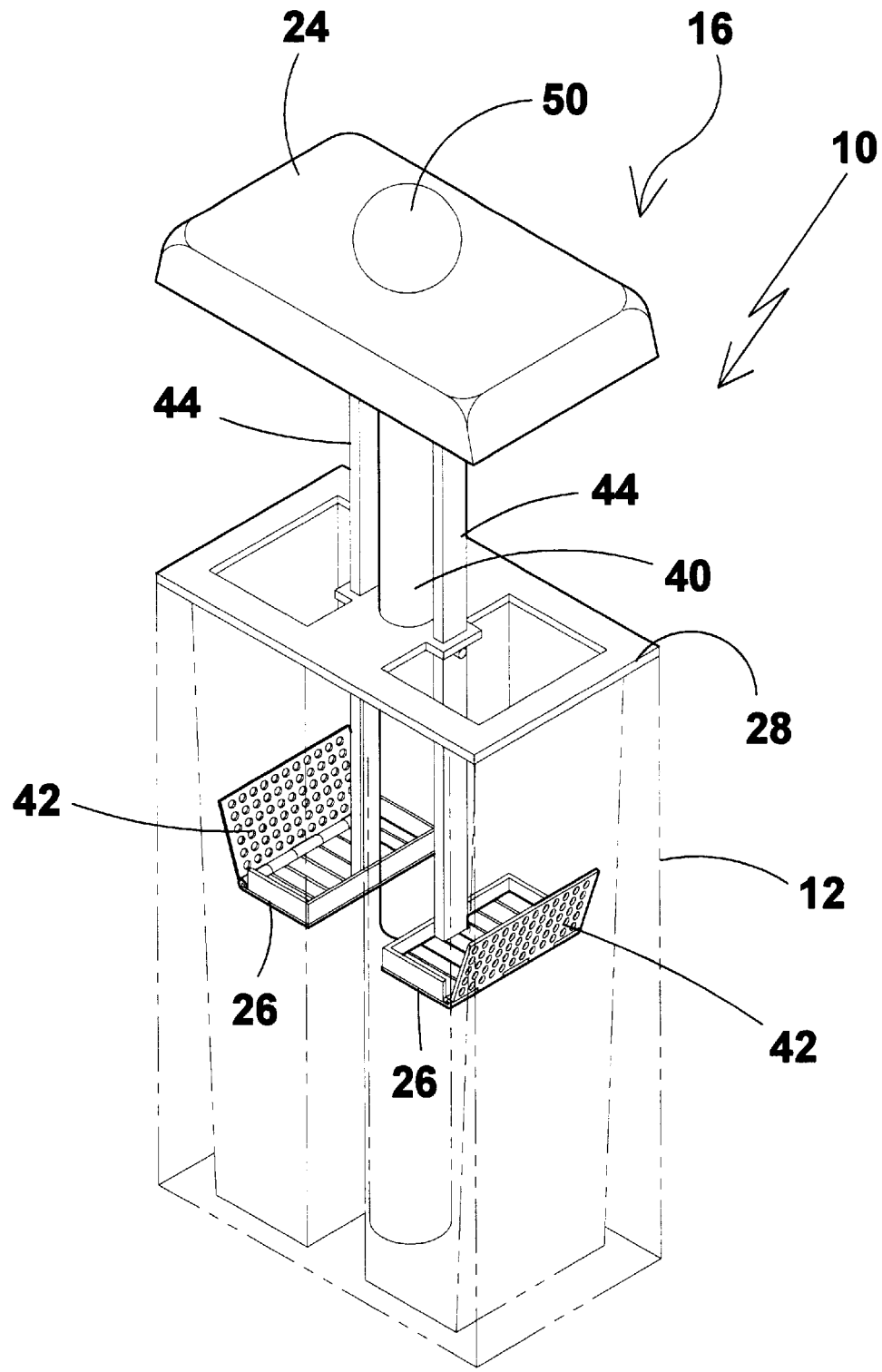
FIG. 4 is a perspective view of the present invention. Shown is the container housing, in outline. The extractor mechanism is raised to a position where the toothbrush platform posts are engaging the slidable extension retention member. The extraction mechanism is comprised of a lid which forms closure means for protecting the contents from particle matter falling into the compartments. In addition there is a central guide post. Also, the extraction mechanism has a plurality of posts equal to the number of compartments within the sanitizing toothbrush holder. Each of these has a pin-like projection for engaging the slidable extension retention member which prevents the toothbrushes from falling out as the extraction mechanism is raised. Each of these post has a toothbrush platform support on the distal end. The hinged toothbrush platform support member will engage the outer housing wall of the toothbrush container while being inserted into or extracted from said sanitizing toothbrush housing member due to the hinged platform.

Turning to FIG. 4, shown therein is a perspective view of the present invention 10 Shown is the container housing 12, in outline. The extractor mechanism 16 is raised to a position where the toothbrush platform posts 44 are engaging the slidable extension retention member 28. Other features previously disclosed are also shown.

Figure 5:
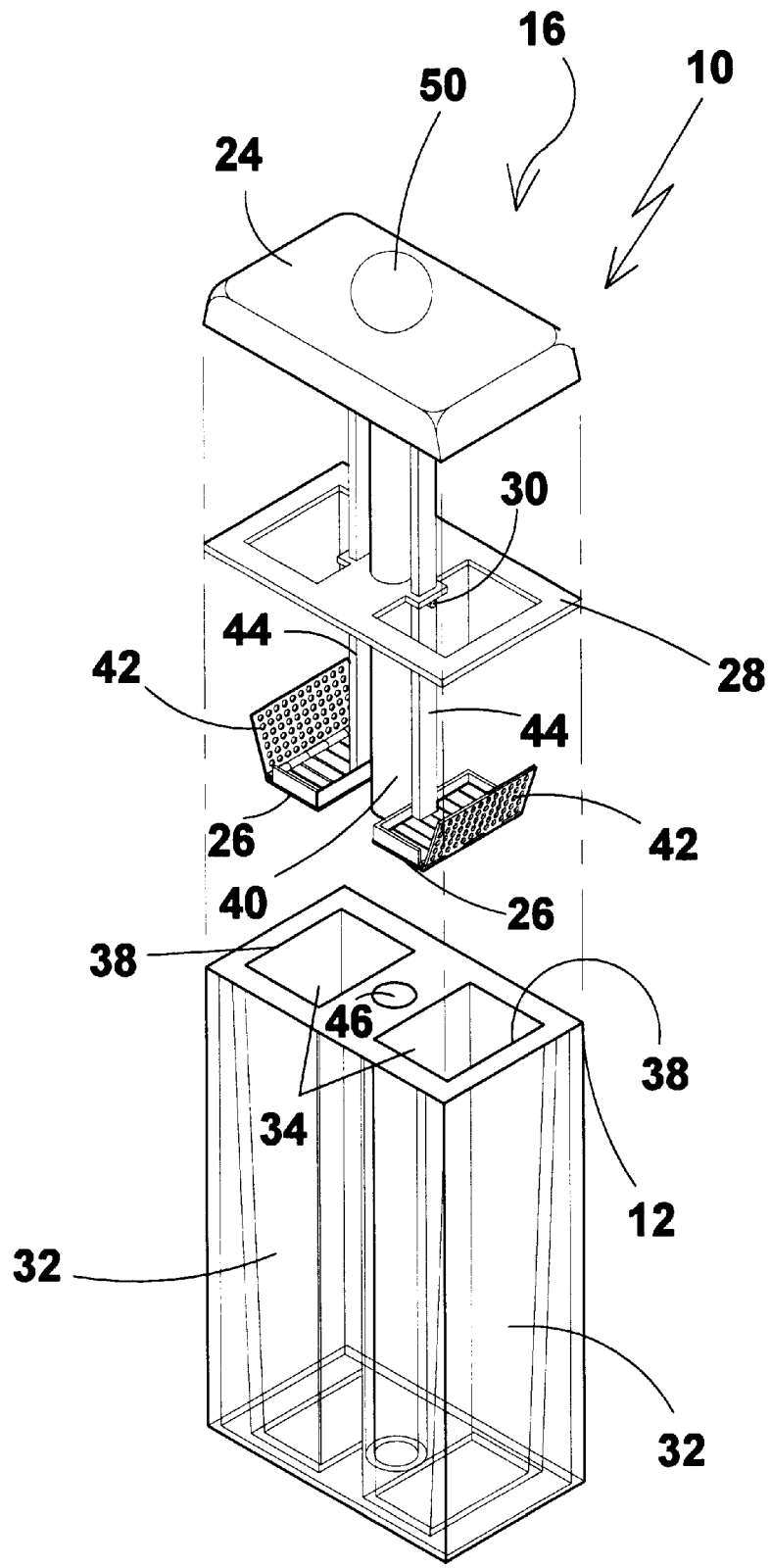
FIG. 5 is an exploded view of the present invention. Shown is the container housing having a plurality of compartments. The individual toothbrush compartments have a tapered annular opening and a smaller tapered base whereby the toothbrushes will diverge from the extraction mechanism while being raised.

Turning to FIG. 5, shown therein is an exploded view of the present invention 10. Shown is the container housing 12 having a plurality of compartments 32. The individual toothbrush compartments 32 have a tapered annular opening 34 and a smaller tapered base 36 whereby the toothbrushes will diverge from the extraction mechanism while being raised.

The extraction mechanism 16 is comprised of a lid 24 with knob 50 which forms closure means for protecting the contents from particle matter falling into the compartments 32. In addition there is a central guide post 40 which is inserted into a central housing aperture 46. Also, the extraction mechanism 16 has a number of posts 44 equal to the number of compartments within the sanitizing toothbrush housing. Each of these has a pin-like projection 30 for engaging the slidable extension retention member frame-like member 28 which prevents the toothbrushes from falling out as the extraction mechanism 16 is raised. Each of these posts 44 has a toothbrush platform support 26 disposed on the distal end. The hinged means 42 of the toothbrush platform support hinge member 26 will engage the outer housing wall 38 while being inserted into or extracted from said sanitizing toothbrush housing but does not fully open.

Turning to FIG. 6, shown therein is a sectional view of the present invention 10. Shown is the sanitizer toothbrush holder having a compartmentalized housing member 12 which forms a receptacle for the extraction mechanism 16. The extraction mechanism 16 is comprised of a lid 24 which forms closure means for protecting the contents from particle matter falling into the compartments 32. Lid 24 has a knob 50 having connecting means 52 thereto. In addition there is a central guide post 40. Also, the extraction mechanism has a plurality of posts 44 equal to the number of compartments 32 within the sanitizing toothbrush holder. Each of these has a pin-like projection 30 for engaging the slidable extension retention member frame-like member 28 which prevents the toothbrushes 18 from falling out as the extraction mechanism is raised. Each of these posts 44 has a toothbrush platform support 26 disposed on the distal end. The hinged means 42 on the toothbrush platform support member 26 will engage the outer housing wall 38 of the toothbrush container while being inserted into or extracted from the sanitizing toothbrush housing member 12 due to the hinged platform 26. The individual toothbrush containers have a tapered annular opening 34 and a smaller tapered base 36 whereby the toothbrushes 18 will diverge from the extraction mechanism while being raised.

Turning to FIG. 7, shown therein is a sectional view of the present invention 10. Shown is the extraction mechanism 16 partially raised from the compartmentalized housing member 12 having the slidable extraction retention member 28 engaged by pin-like projections 30 attached to the toothbrush post 44 of the extraction mechanism. The individual toothbrush platform supports 26 have hinged means 42 for continually engaging the tapered side 38 of the cavity. The hinge 48 will deploy to a fixed position forming a back support for the toothbrush 28 if the extractor mechanism 16 is removed from the container housing 12.

Turning to FIG. 8, shown therein is a perspective view of the present invention 10 having additional elements. Shown is the sanitizing toothbrush holder having a plurality of sanitizing toothbrush compartments 32. Also shown is the extraction mechanism 16 in the partially raised position having a lid 24 which forms closure means for protecting the contents from particle matter falling into the compartments 32. In addition there is a central guide post 40. Also, the extraction mechanism 16 has a plurality of posts 44 equal to the number of compartments 32 within the sanitizing toothbrush holder. Each of these has a pin-like projection 30 for engaging the slidable extension retention member 28 which prevents the toothbrushes 18 from falling out as the extraction mechanism 16 is raised. Each of these posts 44 has a toothbrush platform support 26 on the distal end. The hinged toothbrush platform support member 26 will engage the outer housing wall 38 of the toothbrush container 32 while being inserted into or extracted from said sanitizing toothbrush housing member due to the hinged platform as previously disclosed. The individual toothbrush containers 32 have a tapered annular opening and a smaller tapered base whereby the toothbrushes will diverge from the extraction mechanism while being raised as previously disclosed.

Turning to FIG. 9, shown therein is a perspective view of the present invention 10 having additional elements. Elements are disclosed similar to FIG. 8 and additionally, the container rests on a base member 50 which can be rotated to selectively position a particular toothbrush 18.

What is claimed to be new and desired to be protected by Letters Patent is set forth in the appended claims.

I claim:

1. An apparatus for removably storing toothbrushes in a bath of disinfectant:
   a) a generally upright standing rectangular shaped housing, said housing having at least a pair of cavities therein, said cavities generally rectangular shaped open at the top, said cavities substantially the length of said housing;
   b) said housing having an aperture therein, said aperture centrally vertically disposed intermediate said pair of cavities, said aperture substantially the length of said housing;
   c) an extraction means for the toothbrushes having a rod-like center post disposed in said aperture;
   d) a closure means disposed on said top of said post whereby said housing is covered;
   e) at least a pair of generally horizontal platforms internal said cavities upon which the toothbrushes are rested, said platforms submersible in the bath of disinfectant;
   f) at least a pair of downwardly extending elongated rod-like members communicating between and fixedly attached to said closure means and said platforms;
   g) a frame-like toothbrush retention member, said retention member being complementrally shaped as said cavities, said retention member having at least a pair of openings therein, said openings for receiving said toothbrush handles; and,
   h) stop means provided on said pair of downwardly extending elongated members for receiving and vertically positioning said retention member, said retention member resting on the top of said housing.

2. The apparatus of claim 1, wherein said housing is transparent.

3. The apparatus of claim 1, wherein said cavities have inwardly sloping walls, said cavities being larger at the top than at the bottom.

4. The apparatus of claim 1, said closure means complementrally sized as said top of said housing.

5. The apparatus of claim 4, said closure means further comprising a handle means, said handle means disposed on the top of said closure means.

6. The apparatus of claim 5, said handle means having a means for connection to said closure means.

7. The apparatus of claim 1, wherein said platforms are complementrally shaped as said cavities, said platforms further comprising a three-sided rim for maintaining said toothbrushes therein said rim, further comprising a hinged member mounted thereon, said hinge of said hinged member positioned on the outside edge of said platform.

8. The apparatus of claim 7, wherein said hinged member is complementrally sized as said platforms, said hinged member folding toward the outside of said cavity, said hinged member having one non-hinged edge contiguous to said cavity thereby forming an outer containment wall for said toothbrushes.

9. The apparatus of claim 1, said rod-like members disposed adjacent the inner wall of said cavities wherein the lower end of said elongated rod-like member is connected to the inner edge of said platform.

10. The apparatus of claim 9, said frame-like members further comprising a pair of apertures therein, said apertures for receiving said elongated rod-like members.

11. The apparatus of claim 1, wherein said cavities number two.

12. The apparatus of claim 1, wherein said cavities number four.

* * * * *